United States Patent [19]

Carlyle et al.

[11] 4,447,425
[45] May 8, 1984

[54] MONO- AND BISQUATERNARY AMMONIUM DERIVATIVES OF 2β,16β-DI-AMINO-5α-ANDROSTANE DERIVATIVES AND PHARMACEUTICAL PREPARATIONS CONTAINING SAME

[75] Inventors: Ian C. Carlyle, Hamilton; David S. Savage, Glasgow; Thomas Sleigh, Wishaw, all of Scotland

[73] Assignee: Akzo N.V., Arnhem, Netherlands

[21] Appl. No.: 386,756

[22] Filed: Jun. 9, 1982

[30] Foreign Application Priority Data

Jun. 15, 1981 [GB] United Kingdom ............ 8118365

[51] Int. Cl.³ .................... A61K 31/58; C07J 43/00
[52] U.S. Cl. .................................. 424/241; 260/239.5
[58] Field of Search .................... 260/239.5; 424/241

[56] References Cited

U.S. PATENT DOCUMENTS 4,237,126 12/1980 Carlyle et al. .............. 424/241
4,297,351 10/1981 Carlyle et al. .............. 424/241
4,348,390 9/1982 Kelder .......................... 424/241

Primary Examiner—Elbert L. Roberts
Attorney, Agent, or Firm—Abelman, Frayne, Rezac & Schwab

[57] ABSTRACT

This invention relates to novel mono- and bisquaternary ammonium derivatives of 5α-androstanes having the formula:

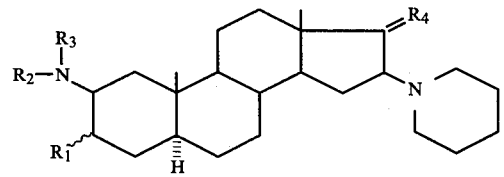

wherein:
$R_1$ = H or alkyl (1–4 C);
$R_2$ and $R_3$ each are alkyl (1–4 C) or form together with the N-atom a piperidino, pyrrolidino or morpholino group;
$R_4$ = O or H($\beta$OR$_5$) and
$R_5$ = H or acyl derived from an organic carboxylic acid having 1–18, preferably 1–6 carbon atoms;

the quaternarizing group being a saturated or unsaturated aliphatic hydrocarbon group having 1–4 carbon atoms the anion being halide; and acid addition salts of the monoquaternary compounds; and to pharmaceutical preparations containing one or more of said androstane compounds as active constituent.

The compounds according to the invention are nondepolarizing neuromuscular blocking agents having very quick onset and recovery characteristics, a short duration of action and a favorable dissociation between muscle blocking and vagal blocking effects.

18 Claims, No Drawings

MONO- AND BISQUATERNARY AMMONIUM DERIVATIVES OF 2β,16β-DI-AMINO-5α-ANDROSTANE DERIVATIVES AND PHARMACEUTICAL PREPARATIONS CONTAINING SAME

This invention relates to novel mono- and bisquaternary ammonium derivatives of 2β,16β-di-amino-5α-androstane derivatives and acid addition salts of the monoquaternary compounds and to pharmaceutical preparations containing one or more of said androstane compounds as active constituent. Also disclosed are processes for their preparation. The invention specifically relates to said androstane derivatives having a 16β-piperidino group next to a 17β-oxygen-containing group.

Quaternary ammonium derivatives of 2β,16β-di-amino-5α-androstanes are known from e.g. British Pat. Nos. 1,138,605 and 1,454,749. See also Journal of Medicinal Chemistry 16, 116–1124, (1973). These compounds have neuromuscular blocking activity. A well-known compound of this type is pancuronium bromide (3α,17β-diacetoxy-2β,16β-dipiperidino-5α-androstane dimethobromide), which has proved a clinically useful non-depolarising muscle relaxant of medium duration of action.

Surprisingly, it was found that novel mono- and bisquaternary ammonium derivatives of 2β,16β-di-amino-5α-androstanes having the formula:

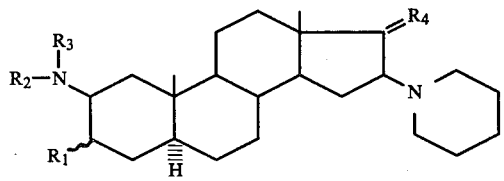

wherein:
$R_1$ = H or alkyl (1–4 C);
$R_2$ and $R_3$ each are alkyl (1–4 C) or form together with the N-atom a piperidino, pyrrolidino or morpholino group;
$R_4$ = O or H(βOR$_5$) and
$R_5$ = H or acyl derived from an organic carboxylic acid having 1–18, preferably 1–6 carbon atoms,
are very potent neuromuscular blocking agents with quick onset and recovery characteristics and a relatively short duration of action. Moreover the novel compounds show a high selectivity, i.e. have a favourable ratio of neuromuscular activity and unwanted vagolytic activity, and neither affect the cardiovascular system, nor release histamine to the same extent as the muscle-relaxant d-tubocurarine.

Therefore, the present invention relates to the above mono- and bisquaternary ammonium derivatives and also extends to pharmaceutical compositions containing a pharmaceutically effective amount of one or more of the novel compounds according to the invention.

The alkyl (1–4 C) group possibly present in position 3 and/or in the 2β-amino group is methyl, ethyl, propyl, isopropyl, butyl or isobutyl and is preferably methyl or ethyl.

The amino group in position 2 is preferably piperidino.

The quaternarising group in the quaternary ammonium derivatives is a saturated or unsaturated aliphatic hydrocarbon group having 1–4 carbon atoms, such as methyl, ethyl, ethynyl, propyl, allyl, propargyl, butyl, isobutyl, and is preferably methyl. The anion in the quaternary ammonium derivatives may in principle be any pharmaceutically acceptable organic or inorganic anion, such as methylsulphonate, p-toluene sulphonate, Cl$^-$, Br$^-$ or I$^-$, and is preferably Br$^-$. In the case of monoquaternary ammonium derivatives the quaternary group may be either in 2β- or in 16β-position and is preferably in 16β-position. The non-quaternarised piperidino group may be converted into the acid addition salt thereof, derived from any pharmaceutically acceptable organic or inorganic acid, such as hydrochloric acid, hydrobromic acid and hydro-iodic acid, nitric acid, sulphuric acid, phosphoric acid, acetic acid, propionic acid, butyric acid, caproic acid, malonic acid, succinic acid, glutaric acid, maleic acid, fumaric acid, tartaric acid, malic acid, pyruvic acid, lactic acid and citric acid.

The compounds according to the invention can be prepared by methods employing steps known or obvious to those skilled in the art.

A suitable starting substance in the case that $R_1$ = H is 2β-hydroxy-5α-androstan-17-one (J.Org.Chem. 30 (1965), 3786).

This 17-oxo compound is reacted with isopropenylacetate/acid yielding 2β,17β-diacetyloxy-5α-androst-16-ene. Reaction of the Δ$^{16}$-compound with a peracid, such as peracetic acid, gives the corresponding 16α,17α-epoxide, which is converted into 2β-acetyloxy-16β-piperidino-5α-androstan-17-one by reaction with piperidine at elevated temperature and preferably in the presence of water. The 2β-amino group is introduced by hydrolysing the 2β-acetyloxy group with alkali to the 2β-hydroxy group, oxidising the 2β-hydroxy group to the 2-oxo group in the usual manner, e.g. with CrO$_3$, and reacting the 2-oxo compound with the amine

in the presence of formic acid to give the corresponding 2β-amino compound.

A suitable starting material for 3-alkylated compounds is for example 3-methyl-5α-androst-2-en-17β-ol acetate (Coll.Czech.Chem.Comm., 1960, 25, 1624). This is hydrolysed to the 17β-ol, which is oxidised with chromium trioxide to the 17-ketone. Treatment with potassium iodate/iodine in acetic acid gives 2β-acetoxy-3α-iodo-3β-methyl-5α-androstan-17-one, from which the 3-iodine atom can be removed with lithium aluminium hydride, after suitably protecting the 17-ketone, e.g. as the ethylene acetal. The 17-oxo compound can then be used for further reaction as indicated above.

For obtaining the 17β-hydroxy compound the 17-oxo compound is reduced with a complex metal hydride, e.g. sodiumborohydride. This reduction may conveniently be performed on 2β-acetyloxy-16β-piperidino-5α-androstan-17-one or the 3-alkyl-analog giving the corresponding 2β-acetyloxy-17β-ol. Hydrolysis with alkali, e.g. sodiumhydroxide, gives the 2β,17β-dihydroxy compound. Before oxidising the 2β-hydroxy group the 17β-hydroxy group is protected by selective acylation, e.g. with acetic acid anhydride in pyridine.

During the amination in 2-position performed after the oxidation step the 17-acyl group is hydrolysed, giving the 2β-amino-(3-alkyl-)16β-piperidino-5α-androstan-17β-ol compound. If desired the 17β-ol can be acylated again in the usual way, e.g. by esterification with a functional derivative of an organic carboxylic acid having 1-18 carbon atoms, preferably 1-6 carbon atoms, such as the acid anhydride or the acid chloride thereof. Preferred organic carboxylic acids include acetic acid, propionic acid, butyric acid, isobutyric acid, trimethylacetic acid.

For obtaining 3α-alkylated compounds the intermediate 17β-acyloxy-3β-alkyl-16β-piperidino-5α-androstan-2-one is epimerised using 20% alcoholic sulphuric acid, giving a mixture of 3β-alkyl- and 3α-alkyl-2-oxo compounds, which are separated by chromatography and then each further reacted with amines.

The quaternary ammonium compounds are obtained by allowing the 2β-amino-16β-piperidino compounds to react with an excess of a saturated or unsaturated aliphatic hydrocarbon halide having 1-4 carbon atoms in a suitable solvent, such as methylene chloride, for several days at room temperature or for several hours at elevated temperature. The monoquaternary compounds can be obtained by reacting the 2β-amino-16β-piperidino compounds with a restricted amount of hydrocarbon halide while reducing the reaction time, and separating the 2β-monoquaternary and/or the 16β-monoquaternary compound from the reaction mixture, e.g. by chromatography or by fractionated crystallisation. Also use can be made of the fact that the 16β-monoquaternary compound is sparingly soluble in certain solvents, e.g. ether. The reaction can then be performed in the presence of such solvent so that the 16β-monoquaternary compound precipitates during the reaction or after the reaction the 16β-monoquaternary compound is precipitated from the reaction mixture by the addition of such solvent. The 2β-monoquaternary can be obtained from the mother liquor by e.g. chromatography on alumina.

The monoquaternary compounds can be converted into the acid addition salts thereof in the usual way by reaction with the pharmaceutically acceptable organic or inorganic acid e.g. in aqueous solution.

The quaternary ammonium compounds according to the invention are intended particularly for use in clinical practice to produce skeletal muscular paralysis during surgical operations.

The compounds are usually administered by intravenous injection, in initial dosages between 5 and 50 mg (bolus injection), followed if necessary by smaller supplementary dosages.

Compounds according to the invention were tested for their neuromuscular and vagal blocking effects in chloralose-anaesthetised cats in comparison with pancuronium bromide.

| Compound | Onset (min.) | Recovery (min.) | Duration (min.) | R |
|---|---|---|---|---|
| Pancuronium Br | 6.2 | 8.3 | 19 | 2.0 |
| Example IIa | 3.7 | 0.5 | 6.1 | 7.0 |
| Example I (16β-yl) | 2.0 | 1.0 | 4.8 | 9.2 |
| Example I (2β-yl) | 2.9 | 1.7 | 8.7 | 7.7 |

R = ratio between neuromuscular blocking activity and vagal blocking activity.

The following examples illustrate the invention.

Example I (a) 5α-Androst-16-ene-2β,17-diol diacetate.

A portion (17.23 ml) of a solution of concentrated sulphuric acid (0.4 ml) in isopropenyl acetate (20 ml) was added dropwise to a solution of 2β-hydroxy-5α-androstan-17-one (27.57 g) in isopropenyl acetate (140 ml). The solvent was removed slowly by distillation through a Vigreux column at such a rate that the solution was concentrated to approx. 60 ml after 6 h. The reaction mixture was cooled in an ice-bath to give a crystalline product, which was filtered off and washed with hexane (300 ml). The crop (33.21 g) in toluene was filtered through a column of silica gel (660 g; 0.2-0.5 mm); the eluate was evaporated to dryness and the residue was crystallised from acetone to afford 5α-androst-16-ene-2β,17-diol diacetate (24.38 g), m.p. 133°-134° C.; $[\alpha]_D + 34.4°$ (c 0.61 in $CHCl_3$).

(b) 16α,17α-Epoxy-5α-androstane-2β,17β-diol diacetate.

Anhydrous sodium acetate (3.73 g) was added to a solution of 5α-androst-16-ene-2β,17β-diol diacetate (37.3 g) in chloroform (190 ml) and the suspension was cooled in an ice-bath. Peracetic acid (37.3 ml; 40% m/m) was added dropwise to the stirred suspension, maintaining the temperature between 0°-5° C. After 3.25 h, water (200 ml) was added and the organic layer was separated, washed neutral with water (4×200 ml) and dried ($MgSO_4$). The solution was evaporated to dryness and the residue was crystallised from diethyl ether to give 16α,17α-epoxy-5α-androstane-2β,17β-diol diacetate (31.87 g), m.p. 162°-164° C.; $[\alpha]_D + 11.4°$ (c 0.64 in $CHCl_3$).

(c) 2β-Acetyloxy-16β-(1-piperidinyl)-5α-androstan-17-one.

A solution of 16α,17α-epoxy-5α-androstane-2β,17β-diol diacetate (31.87 g) in a mixture of piperidine (192 ml) and water (19.2 ml) was heated under reflux for 1 h. The solution was evaporated to dryness under reduced pressure and the residual gum was taken up in dichloromethane (200 ml). The solution was dried ($MgSO_4$) and evaporated to dryness to yield 2β-acetyloxy-16β-(1-piperidinyl)-5α-androstan-17-one as an uncrystallisable, pale yellow gum (33.61 g).

(d) 16β-(1-Piperidinyl)-5α-androstane-2β,17β-diol 2-acetate.

Sodium borohydride (9.40 g) was added portionwise to a stirred solution of 2β-acetyloxy-16β-(1-piperidinyl)-5α-androstan-17-one (46.99 g) in methanol (235 ml). After 1 h, water (300 ml) was added to precipitate the product as a gum, which was extracted into diethyl ether (300 ml). The extract was washed neutral with water (3×300 ml), dried ($MgSO_4$) and evaporated to dryness. Crystallisation of the residue from methanol afforded 16β-(1-piperidinyl)-5α-androstane-2β,17β-diol 2-acetate (25.49 g), m.p. 162°-166° C., $[\alpha]_D + 29.1°$ (c 0.45 in $CHCl_3$).

(e) 16β-(1-Piperidinyl)-5α-androstane-2β,17β-diol.

Sodium hydroxide solution (60 ml; 4N) was added to a solution of 16β-(1-piperidinyl)-5α-androstane-2β,17β-diol 2-acetate (25.49 g) in methanol (120 ml) and the mixture was heated under reflux for 1 h. When the solution had cooled to room temperature, water (200 ml) was added to precipitate the product, which was filtered off and washed with water (3×200 ml). A solution of the crude solid in diethyl ether (150 ml) was washed neutral with water (2×200 ml), dried ($MgSO_4$) and evaporated to dryness. Crystallisation of the resulting white solid from methanol acetone afforded 16β-(1-piperidinyl)-5α-androstane-2β,17β-diol (17.51 g), m.p. 215°–219° C.; $[\alpha]_D + 36.1°$ (c 0.48 in CHCH₃).

(f) 16β-(1-Piperidinyl)-5α-androstane-2β,17β-diol 17-acetate.

Acetic anhydride (5.25 ml) was added dropwise to a stirred solution of 16β-(1-piperidinyl)-5α-androstane-2β,17β-diol (14.0 g) in pyridine (280 ml) maintaining the temperature below 5° C. by means of an ice-bath. When the addition was complete, the cooling bath was removed. After 2 h, saturated sodium carbonate solution (approx. 120 ml) was added to give pH >7 and the precipitated product was extracted into dichloromethane (100 ml). The extract was washed with water (3×200 ml), dried (MgSO₄) and evaporated to dryness. Crystallisation of the residue from acetone afforded 16β-(1-piperidinyl)-5α-androstane-2β,17β-diol 17-acetate (14.38 g), m.p. 239°–240° C.; $[\alpha]_D + 25.5°$ C. (c 0.53 in CHCl₃).

(g) 17β-Acetyloxy-16β-(1-piperidinyl)-5α-androstan-2-one

Jones reagent (21.0 ml; 8N) was added dropwise to a stirred suspension of 16β-(1-piperidinyl)-5α-androstane-2β,17β-diol 17-acetate (14.0 g) in acetone (250 ml), cooled to approx. 5° C. in an ice-bath. When the addition was complete, the cooling bath was removed and stirring was continued for 3 h. Saturated sodium carbonate solution (100 ml) was added to give pH approx. 9 and the product was extracted into dichloromethane (150 ml). The organic layer was separated, washed neutral with water (3×150 ml) and dried (MgSO₄). The solution was concentrated while ether was added to afford 17β-acetyloxy-16β-(1-piperidinyl)-5α-androstan-2-one (12.2 g) m.p. 165°–167° C.; $[\alpha]_D + 44.6°$ (c 0.45 in CHCl₃).

(h) 2β,16β-di-(1-piperidinyl)-5α-androstan-17β-ol.

A solution of 17β-acetyloxy-16β-(1-piperidinyl)-5α-androstan-2-one (8.24 g) in piperidine (36 ml) and formic acid (12 ml) was heated at reflux temperature under a nitrogen (oxygen-free) atmosphere for 4.5 h. When the solution had cooled to room temperature, water (50 ml) was added to precipitate the product, which was filtered off and washed well with water (300 ml). A solution of the crude product in diethyl ether (60 ml) was washed with water (2×100 ml), dried (MgSO₄) and evaporated to dryness. Crytsllisation of the residue from acetone afforded 2β,16β-di-(1-piperidinyl)-5α-androstan-17β-ol (4.17 g), m.p. 176°–181° C.; $[\alpha]_D + 41.3°$ (c 0.59 in CHCl₃).

(i) 2β,16β-di-(1-piperidinyl)-5α-androstan-17β-ol acetate.

Acetic anhydride (1.21 ml) was added to a solution of 2β,16β-di-(1-piperidinyl)-5α-androstan-17β-ol (3.77 g) in dry pyridine (75 ml) at 0°–5° C. and the solution was set aside at room temperature for 19 h. Saturated sodium carbonate solution (40 ml) was added to precipitate the product, which was filtered off and washed well with water (200 ml). A solution of the crude product in diethyl ether (50 ml) was washed with water (2×100 ml), dried (MgSO₄) and concentrated to afford 2β,16β-di-(1-piperidinyl)-5α-androstan-17β-ol acetate (3.91 g), m.p. 156°–161° C.; $[\alpha]_D + 28.7°$ (c 0.47 in CHCl₃).

(j) 1-[17β-acetyloxy-2β-(1-piperidinyl)-5α-androstan-16β-yl]-1-methyl-piperidinium bromide.

Bromoethane (1.5 g) was added to a solution of 2β,16β-di-(1-piperidinyl)-5α-androstan-17β-ol acetate (1.0 g) in a mixture of dry dichloromethane (10 ml) and dry diethyl ether (10 ml). The solution was sealed in a pressure bottle and set aside at room temperature for 7.5 h. The solvent was then removed under reduced pressure, without heating, to afford a white solid, which was dissolved in the minimum of dry dichloromethane (8.0 ml) and dry diethyl ether (30 ml) was added to precipitate the crude product (0.3 g). The material from the mother liquor was retreated with bromomethane (1.05 g) in dry dichloromethane (7.0 ml) and dry diethyl ether (7.0 ml), as above, to yield a further quantity (0.3 g) of crude product. The procedure was repeated once again to obtain a final amount (0.25 g) of crude product. The three crops were combined and crystallised from dichloromethaneacetone to afford 1-[17β-acetyloxy-2β-(1-piperidinyl)-5α-androstan-16β-yl]-1-methyl-piperidinium bromide (0.30 g), m.p. 213°–219° C.; $[\alpha]_D - 19.5°$ (c 0.36 in CHCl₃).

Careful chromatography of the material from the mother liquors on acid-washed alumina yielded the alternative monoquaternary compound, 1-[17β-acetyloxy-16β-(1-piperidinyl)-androstan-2β-yl]-1-methyl-piperidinium bromide, m.p. 206°–211° C.; $[\alpha]_D^{20} = +73°$ (c 1.2 in CH₂Cl₂), and a small amount of the bisquaternary compound (see Example II).

Example II (a) 1,1'-[17β-acetyloxy-androstane-2β,16β-diyl]bis[1-methyl-piperidinium]dibromide.

Bromomethane (2.0 g) was added to a solution of 2β,16β-di-(1-piperidinyl)-5α-androstan-17β-ol acetate (1.0 g) in dry dichloromethane (20 ml) and the solution was sealed in a pressure bottle. After 2.5 d, the mixture was evaporated without heating to afford a white solid (1.1 g). Chromatography of a solution of the crude product in ethyl acetate isopropanol (3:1) on acid-washed alumina (44 g; grade H) removed the front running impurities (monoquaternary compounds). Elution with ethyl acetate-isopropanol (2:1) and recrystallisation of the resulting material from dichloromethane-ether gave pure 1,1'-[17β-acetyloxy-5α-androstane-2β,16β-diyl]bis[1-methyl-piperidinium]dibromide (1.0 g), m.p. 204°–209° C.; $[\alpha]_D + 20°$ (c 0.47 in H₂O).

(b) Bis(1-allyl-piperidinium) compounds

Using in Example II(a) allylbromide instead of bromomethane gave 1,1'-[17β-acetyloxy-5α-androstane-2β,16β-diyl]bis[1-allyl-piperidinium]dibromide.

Example III

17-Hydroxy compounds

The 17-hydroxy compound of Example I(h) was converted in a similar way as described in Example I(j) and Example II into the corresponding 16β-monoquaternary, the corresponding 2β-monoquaternary and the corresponding 2β,16β-bisquaternary compound, respectively.

Example IV

17-Oxo compounds

The 17-oxo compound of Example I(c) was hydrolysed in 2-position as described in Example I(e) and then oxidised in 2-position as described in Example I(g). Amination as described in Example I(h) gave 2β,16β-di-(1-piperidinyl)-5α-androstan-17-one, which was converted in a similar way as described in Example I(j) and Example II into the corresponding 16β-mono-quaternary, the corresponding 2β-mono-quaternary and the corresponding 2β,16β-bisquaternary compound, respectively. The monoquaternary compounds were converted into their acid addition salts derived from hydrochloric acid and citric acid, respectively.

Example V

Various 2β-amino compounds

In a similar way as described in Examples I(h) 17β-acetyloxy-16β-(1-piperidinyl)-5α-androstan-2-one was aminated with morpholine, pyrrolidine and dimethylamine respectively, and the diamino compounds thus obtained were quaternarised in a similar way as described in Example I(i) and (j), Example II or Example III. Monoquaternary compounds were converted into their acid addition salts.

Example VI

3-Alkylated compounds (a) 3-Methyl-5α-androst-2-en-17β-ol

Aqueous sodium hydroxide solution (50 ml; 4N) was added to a solution of 3-methyl-5α-androst-2-en-17β-ol acetate (50 g) in methanol (400 ml) and the solution was heated under reflux for 1 h. The solution was cooled and water was added to precipitate the product (43 g). Recrystallisation of a sample from ether gave pure 3-methyl-5α-androst-2-en-17β-ol, m.p. 128°–130°; $[\alpha]_D + 68°$ (c 0.31 in EtOH).

(b) 3-Methyl-5α-androst-2-en-17-one

Kiliani's reagent (100 ml) was added slowly to a solution of 3-methyl-5α-androst-2-en-17β-ol (43 g) in acetone (170 ml). When the addition was complete, water was added to give a precipitate, which was filtered off. The product was redissolved in acetone and water was again added. The precipitate was filtered off, washed with water and dried to give 3-methyl-5α-androst-2-en-17-one (35.7 g). A sample was recrystallised from ether-light petroleum (40°–60°) and from ether to give pure material, m.p. 124°–126°; $[\alpha]_D + 141°$ (c 0.48 in EtOH).

(c) 2β-Acetyloxy-3α-iodo-3β-methyl-5α-androstan-17-one

Iodine (47 g) and potassium iodate (18 g) were added to a solution of 3-methyl-5α-androst-2-en-17-one (100 g) in glacial acetic acid (3 l) and the mixture was stirred at 60° C. for 1.5 h. The mixture was cooled to room temperature, water (2.5 l) was added and the product was extracted into diethyl ether. The extract was washed with potassium bicarbonate solution (1 l), sodium sulphite solution (500 ml) and finally with water (3×1 l) to neutrality. The organic layer was dried (MgSO$_4$) and concentrated to yield 2β-acetyloxy-3α-iodo-3β-methyl-5α-androstan-17-one as a colourless solid (94.03 g).

(d) 2β-Acetyloxy-3α-iodo-3β-methyl-5α-androstan-17-one cyclic 1,2-ethanediyl acetal 4-Methyl-benzensulphonic acid (5.7 g) was added to a stirred suspension of 2β-acetyloxy-3α-iodo-3β-methyl-5α-androstan-17-one (57.39 g) in a mixture of 1,2-ethane diol (115 ml) and triethyl orthoformate (115 ml). After 10 min., complete solution was achieved, followed by precipitation of the product, which was fully precipitated by the addition of water (200 ml). The product was filtered off, washed with water (3×500 ml) and taken up in diethyl ether (300 ml). The solution was dried (MgSO$_4$) and evaporated to dryness to give a white solid, which was recrystallised from light petroleum (40°–60°) to afford 2β-acetyloxy-3α-iodo-3β-methyl-5α-androstan-17-one cyclic 1,2-ethanediyl acetal (52.3 g).

(e) 2β-Hydroxy-3β-methyl-5α-androstan-17-one cyclic 1,2-ethanediyl acetal

A solution of 2β-acetyloxy-3α-iodo-3β-methyl-5α-androstan-17-one cyclic 1,2-ethanediyl acetal (61.7 g) in tetrahydrofuran (1 l) was added to an ice-cold suspension of lithium aluminium hydride (12.34 g) in tetrahydrofuran (2 l), and the resulting mixture was heated, with stirring, under reflux for 0.5 h. The reaction mixture was cooled in an ice-bath, water (3 ml) was added cautiously, dropwise, followed by sodium hydroxide solution (3 ml; 4N) and the resulting suspension was filtered through a dicalite pad to remove the inorganic material. The pad was washed with hot tetrahydrofuran (500 ml) and the filtrate was evaporated to dryness. The residue was dissolved in dichloromethane (200 ml) and the solution was dried (MgSO$_4$) and evaporated to dryness to give a white solid, which was recrystallised from acetone to afford 2β-hydroxy-3β-methyl-5α-androstan-17-one cyclic 1,2-ethanediyl acetal (34.7 g).

(f) 2β-Hydroxy-3β-methyl-5α-androstan-17-one

A solution of 2β-hydroxy-3β-methyl-5α-androstan-17-one cyclic 1,2-ethanediyl acetal (42.1 g) in glacial acetic acid (210 ml) and water (21 ml) was heated on a water-bath for 10 min. Water (300 ml) was added to the cooled solution to precipitate the product, which was filtered off, washed with water (3×500 ml) and taken up in diethyl ether (300 ml). The solution was washed with saturated sodium carbonate solution (2×250 ml) and water (2×300 ml), dried (MgSO$_4$) and concentrated to yield 2β-hydroxy-3β-methyl-5α-androstan-17-one (25.49 g).

In a similar way as described in Example I(a)–(g) 2β-hydroxy-3β-methyl-5α-androstan-17-one was converted into 17β-acetyloxy-3β-methyl-16β-(1-piperidinyl)-5α-androstan-2-one.

(h) Epimerisation of 17β-acetyloxy-3β-methyl-16β-(1-piperidinyl)-5α-androstan-2-one 17β-Acetyloxy-3β-methyl-16β-(1-piperidinyl)-5α-androstan-2-one (20.0 g) was added portionwise to a solution of sulphuric acid (10.9 ml) in methanol (100 ml) and the solution was stirred at room temperature for 1 h. Water was added and the product was extracted with diethyl ether. The extract was washed with water, sodium bicarbonate solution and with water to neutrality, dried (MgSO$_4$) and evaporated to give a pale yellow gum (19.6 g), which was dissolved in ether and chromatographed on acid-washed alumina (200 g). Elution with ether-ethyl acetate 9:1 gave recovered 17β-acetyloxy-3β-methyl-16β-(1-piperidinyl)-5α-androstan-2-one (9.1 g), followed by the 3α-isomer (7.3 g), which was crystallised from ether.

(i) 3β-Methyl-2β,16β-di-(1-piperidinyl)-5α-androstan-17β-ol

17β-Acetyloxy-3β-methyl-16-(1-piperidinyl)-5α-androstan-2-one was treated with piperidine and formic acid, as described in Example I(h), to give 3β-methyl-2β,16β-di-(1-piperidinyl)-5α-androstan-17β-ol.

Similarly prepared were:
3β-methyl-2β-(4-morpholinyl)-16β-(1-piperidinyl)-5α-androstan-17β-ol;
3β-methyl-2β-diethylamino-16β-(1-piperidinyl)-5α-androstan-17β-ol;
3α-methyl-2β,16β-di-(1-piperidinyl)-5α-androstan-17β-ol;
3α-methyl-2β-(4-morpholinyl)-16β-(1-piperidinyl)-5α-androstan-17β-ol;
3α-methyl-2β-diethylamino-16β-(1-piperidinyl)-5α-androstan-17β-ol.

(j) The 3-methyl-17β-alcohols of Example VI(i) were acetylated as described in Example I(i).

(k) Monoquaternary and bisquaternary ammonium compounds of the compounds of Example VI(g), (i) and (j) were prepared in a similar way as described in Examples I(j), II and III. Monoquaternaries were converted in their acid addition salts.

(l) In a similar way as described in Example IV 2β-acetyloxy-3β-methyl-16β-(1-piperidinyl)-5α-androstan-17-one was hydrolysed, oxidised and aminated in position 2 to give similar compounds as in Example I(k). Monoquaternaries were converted into their acid addition salts.

We claim:

1. Mono- and bisquaternary ammonium derivatives of 2β,16β-di-amino-5α-androstanes having the formula:

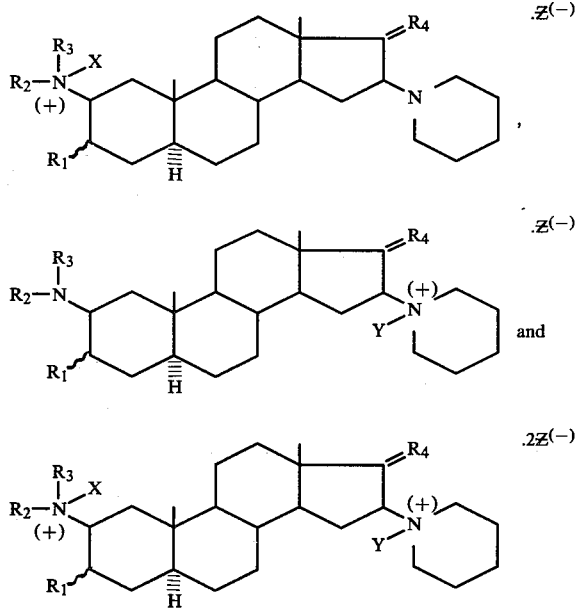

wherein:
$R_1$ = H or alkyl (1–4 C);
$R_2$ and $R_3$ each are alkyl (1–4 C) or form, together with the N-atom, a piperidino, pyrrolidino or morpholino group;
$R_4$ = O or H($\beta OR_5$) and
$R_5$ = H or ($C_1$–$C_{18}$) acyl, X and Y are the same or different and are a saturated or unsaturated aliphatic hydrocarbon group having 1–4 carbon atoms, $Z^{(-)}$ is a halide, and the acid addition salts of the monoquaternary compounds.

2. A compound according to claim 1, wherein $R_1$ = H or methyl.

3. A compound according to claim 1 or 2, wherein $R_2$ and $R_3$ each are methyl or ethyl.

4. A compound according to claim 1 or 2, wherein $R_2$ and $R_3$ together with the N-atom represent piperidino.

5. A compound according to claims 1 or 2, wherein $R_4$ = H($\beta OR_5$) and $R_5$ = acetyl.

6. A compound according to claims 1 or 2, wherein x and y are each a methyl group.

7. A compound according to claims 1 or 2, wherein $Z^-$ is $Br^-$.

8. A pharmaceutical composition having neuromuscular blocking activity comprising a neuromuscular blocking effective amount of one or more compounds of claim 1 and a pharmaceutically acceptable carrier.

9. A compound according to claim 3, wherein $R_4$ = H($\beta OR_5$) and $R_5$ = acetyl.

10. A compound according to claim 3, wherein the quaternarising group is a methyl group.

11. A compound according to claim 3, wherein the halide anion is $Br^-$.

12. A compound according to claim 4, wherein $R_4$ = H($\beta OR_5$) and $R_5$ = acetyl.

13. A compound according to claim 4, wherein the quaternarising group is a methyl group.

14. A compound according to claim 4, wherein the halide anion is $Br^-$.

15. A compound according to claim 5, wherein the quaternarising group is a methyl group.

16. A compound according to claim 5, wherein the halide anion is $Br^-$.

17. A compound according to claim 6, wherein the halide anion is $Br^-$.

18. A compound according to claim 1, wherein $R_5$ is ($C_1$–$C_6$) acyl.

* * * * *